(12) United States Patent
Node et al.

(10) Patent No.: US 8,900,815 B2
(45) Date of Patent: Dec. 2, 2014

(54) PLATELET-DERIVED MICROPARTICLES AS A NOVEL DIAGNOSIS MAKER FOR A CARDIOVASCULAR DISEASE

(75) Inventors: Koichi Node, Takarazuka (JP); Teruo Inoue, Saitama (JP)

(73) Assignee: Saga University, Saga (JP)

( * ) Notice: Subject to any disclaimer, the term of this patent is extended or adjusted under 35 U.S.C. 154(b) by 856 days.

(21) Appl. No.: 11/883,447

(22) PCT Filed: Feb. 21, 2005

(86) PCT No.: PCT/IB2005/000422
§ 371 (c)(1),
(2), (4) Date: Jul. 31, 2007

(87) PCT Pub. No.: WO2006/087597
PCT Pub. Date: Aug. 24, 2006

(65) Prior Publication Data
US 2008/0248488 A1 Oct. 9, 2008

(51) Int. Cl.
*G01N 33/53* (2006.01)
*C12Q 1/00* (2006.01)
*G01N 33/86* (2006.01)

(52) U.S. Cl.
CPC .................................... *G01N 33/86* (2013.01)
USPC ................................................ 435/7.1; 435/4

(58) Field of Classification Search
CPC .............. A61K 35/12; A61K 38/1709; A61K 49/0004; G01N 2800/325; G01N 2800/32; G01N 2800/324
See application file for complete search history.

(56) References Cited

U.S. PATENT DOCUMENTS 5,552,290 A * 9/1996 Michelson et al. .......... 435/7.21
2003/0175831 A1 9/2003 Canton et al.

FOREIGN PATENT DOCUMENTS

| JP | 2003-533698 A | 11/2003 |
| JP | 2004-520598 A | 7/2004 |
| JP | 2005-30824 A | 2/2005 |
| WO | WO 02/089657 A2 | 11/2002 |

OTHER PUBLICATIONS

Flaumenhaft. 2006. Blood Cells, Molecules and Diseases 36:182-187.*
American Heart Association, the Role of C-Reactive Protein, www.americanheart.org/print_presenter.jhtml;jsessionid=Z5EJTPVDLPI1GCQFCX, downloaded Jul. 31, 2009).*
Lin et al. 2007. Nephrol. Dial. Transpl 23:1642-9.*
American Heart Association, Risk Factors and Coronary Heart Disease, www.americanheart.org/print_presenter.jhtml;jsessionid=KKKCF5CM225XGUCQFC, downloaded Jul. 30, 2009).*
Heart Disease Guide, www.webmd.com/heart-disease-symptoms, downloaded Jul. 31, 2009.*
Li et al. 2001. Angiology 53:265-272.*
Craft et al. 2003. Blood Coagul and Fibrinolysis. 14:719-728).*
Li 1999. Cell Research 9:171-178.*
Peripheral Artery Disease and Intermittent Claudication, www.umm.edu/cgi-bin, downloaded Aug. 2, 2009.*
Singh et al 1995. Can J. Cardiol 11:1015-1021.*
Dehmer et al 1997. Am J of Cardiol. 80:871-877.*
2004. Medical Encyclopedia, Medline Plus, http://www.nlm.nih.gov/medlineplus/ency/article/000198.htm, downloaded Jan. 24, 2014.*
Nomura, Shosaku, "Function and Clinical Significance of Platelet-Derived Microparticles," International Journal of Hematology, 74 (2001), pp. 397-404.
Sims, Peter J., et al., "Complement Proteins C5b-9 Cause Release of Membrane Vesicles from the Platelet Surface That Are Enriched in the Membrane Receptor for Coagulation Factor Va and Express Prothrombinase Activity," The Journal of Biological Chemistry, vol. 263, No. 34, Issue of Dec. 5, pp. 18205-18212, 1988.
Barry, Orla P., et al., "Modulation of Monocyte-Endothelial Cell Interactions by Platelet Microparticles," J. Clin. Invest., vol. 102, No. 1, Jul. 1998, pp. 136-144.
Osumi, Kazuoki, et al., "Development and Assessment of Enzyme Immunoassay for Platelet-derived Microparticles," Thromb Haemost 2001; 85: pp. 326-330.
Cole, C. William, "Association of polymorphonuclear leukocytes with sites of aortic catheter-induced injury in rabbits," Atherosclerosis, 67 (1987), pp. 229-236.
Deservi, S., et al., "Granulocyte activation after coronary angioplasty in humans," Circulation, 1990; 82: pp. 140-146.
Kuijper, Ph, et al., "Platelet-dependent primary hemostasis promotes selectin- and integrin-mediated neutrophil adhesion to damaged endothelium under flow conditions," Blood, 1996, 87: pp. 3271-3281.
Hagberg, Inger Anne, et al., "Adhesion of Leukocytes to Growing Arterial Thrombi," Thromb Haemost, 1998, 80: pp. 852-858.
Diacovo, TG, et al., "Neutrophil rolling, arrest, and transmigration across activated, surface-adherent platelets via sequential action of P-selectin and the beta 2-integrin CD11b/CD18," Blood, 1996, 88: pp. 146-157.
Simon, Daniel I., et al., "Platelet Glycoprotein Ibα is a Counterreceptor for the Leukocyte Integrin Mac-1 (CD11b/CD18)," J. Exp. Med., vol. 192, No. 2, Jul. 17, 2000, pp. 193-204.
Rogers, Campbell, et al., "A mAb to the $\beta_2$-leukocyte integrin Mac-1 (CD11b-CD18) reduces intimal thickening after angioplasty or stent implantation in rabbits," Proc. Natl. Acad. Sci. USA, vol. 95, pp. 10134-10139, Aug. 1998.
Simon, Daniel I., et al., "Decreased neointimal formation in Mac-1$^{-/-}$ mice reveals a role for inflammation in vascular repair after angioplasty," J. Clin. Invest., 105: pp. 293-300 (2000).

(Continued)

*Primary Examiner* — Shulamith H Shafer
(74) *Attorney, Agent, or Firm* — Birch, Stewart, Kolasch & Birch, LLP (57) ABSTRACT

The present invention is directed to a method for evaluating whether coronary artery disease has progressed in a patient previously diagnosed as having the disease, wherein the method includes: (a) obtaining a biological sample from the patient at a first time point and a second time point; (b) detecting the level of platelet-derived microparticles (PD-MPs) or a fragment thereof, in the first time point sample and the second time point sample with an antibody to PDMPs or a fragment thereof; wherein an increase in a level of the PDMPs in the second time point sample in comparison to a level in the first time point sample is indicative of progression of coronary artery disease.

4 Claims, 3 Drawing Sheets

(56) References Cited

OTHER PUBLICATIONS

Neumann, Franz-Josef, et al., "Neutrophil and Platelet Activation at Balloon-Injured Coronary Artery Plaque in Patients Undergoing Angioplasty," JACC, vol. 27, No. 4, Mar. 15, 1996, pp. 819-824.

Inoue, Teruo, et al., "Expression of Polymorphonuclear Leukocyte Adhesion Molecules and Its Clinical Significance in Patients Treated With Percutaneous Transluminal Coronary Angioplasty," JACC, vol. 28, No. 5, Nov. 1, 1996, pp. 1127-1133.

Inoue, Teruo, et al., "Clinical Significance of Neutrophil Adhesion Molecules Expression after Coronary Angioplasty on the Develpoment of Restenosis," Thromb Haemost, 1998; 79: pp. 54-58.

Inoue, Teruo, et al., "Lower Expression of Neutrophil Adhesion Molecule Indicates Less Vessel Wall Injury and Might Explain Lower Restenosis Rate After Cutting Balloon Angioplasty," Circulation, 1998; 97: pp. 2511-2518.

Inoue, Teruo, "Comparison of Activation Process of Platelets and Neutrophils After Coronary Stent Implantation Versus Balloon Angioplasty for Stable Angina Pectoris," Am. J. Cardiol, 2000; 86: pp. 1057-1062.

Inoue, Teruo, et al., "Stent-Induced Expression and Activation of the Leukocyte Integrin Mac-1 is Associated With Neointimal Thickening and Restenosis," Circulation, 2003; 107: pp. 1757-1763.

Ledue, Thomas B., et al., "Analytical evaluation of particle-enhanced immunonephelometric assays for C-reactive protein, serum amyloid A and mannose-binding protein in human serum," Ann Clin Biochem, 1998; 35: pp. 745-753.

Elemer, GS, et al., "Two independent sets of monoclonal anitbodies define neoepitopes linked to soluble ligand binding and leukocyte adhesion functions of activated alpha M beta 2," Circulation Research, 1994; 75: pp. 165-171.

Zucker-Franklin, Dorothea, et al., "Red-Cell and Platelet Fragmentation in Idiopathic Autoimmune Thrombocytopenic Purpura," The New England Journal of Medicine, Sep. 8, 1977, vol. 297, No. 10, pp. 517-523.

Lee, Young J., et al., "Elevated Platelet Microparticles in Transient Ischemic Attacks, Lacunar Infarcts, and Multiinfarct Dementias," Thrombosis Research, vol. 72, 1993, pp. 295-304.

Katopodis, John N., et al., "Platelet Microparticles and Calcium Homeostasis in Acute Coronary Ischemias," American Journal of Hematology, vol. 54, pp. 95-101, 1997.

Nomura, Shosaku, et al., "Platelet-Derived Microparticles in Patients with Arteriosclerosis Obliterans: Enhancement of High Shear-Induced Microparticle Generation by Cytokines, " Thrombosis Research, vol. 98, 2000, pp. 257-268.

Gawaz, Meinrad, et al., "Platelet Function in Acute Myocardial Infarction Treated With Direct Angioplasty," Circulation, 1996, vol. 93, No. 2, pp. 229-237.

Nomura, Shosaku, et al., "Enzyme immunoassay detection of platelet-derived microparticles and RANTES in acute coronary syndrome," Thromb Haemost, 2003, vol. 89, pp. 506-512.

Springer, Timothy A., "Traffic Signals for Lymphocyte Recirculation and Leukocyte Emigration: The Multistep Paradigm," Cell, vol. 76, pp. 301-314, Jan. 28, 1994.

Evangelista, Virgilio, et al., "Platelet/Polymorphonuclear Leukocyte Interaction in Dynamic Conditions: Evidence of Adhesion Cascade and Cross Talk Between P-Selectin and the $\beta 2$ Integrin CD11b/CD18," Blood, vol. 88, No. 11, Dec. 1, 1996, pp. 4183-4194.

Evangelista, Virgilio, et al., "Platelet/Polymorphonuclear Leukocyte Interaction: P-Selectin Triggers Protein-Tyrosine Phosphorylation-Dependent CD11b/CD18 Adhesion: Role of PSGL-1 as a Signaling Molecule," Blood, vol. 93, No. 3, Feb. 1, 1999, pp. 876-885.

Santoso, Sentot, et al., "The Junctional Adhesion Molecule 3 (JAM-3) on Human Platelets is a Counterreceptor for the Leukocyte Integrin Mac-1," J. Exp. Med., vol. 196, No. 5, Sep. 2, 2002, pp. 679-691.

Forlow, Stephen B., et al., "Leukocyte-leukocyte interactions mediated by platelet microparticles under flow," Blood, vol. 95, No. 4, Feb. 15, 2000, pp. 1317-1323.

Ando et al., "Circulating platelet-derived microparticles with procoagulant activity may be a potential cause of thrombosis in uremic pateints," Kidney International, vol. 62, No. 5, 2002, XP002356263, ISSN: 0085-2538, pp. 1757-1763.

Abrams et al., "Direct Detection of Activated Platelets and Platelet-Derived Microparticles in Humans," Blood, vol. 75, No. 1, 1990, XP000564281, ISSN: 0006-4971, pp. 128-138.

Tan et al., "Platelet microparticles and the relationship to the severity of atherosclerotic vascular disease," European Heart Journal, vol. 25, 2004, XP002356264, ISSN: 0195-668X, pp. 348.

Japanese Office Action, Appl. No. 2007-555714, Jun. 29, 2010, pp. 1-3 (with full English translation).

JPO Office Action (Decision of Rejection), Appl. No. 2007-555714, Mar. 1, 2011, pp. 1-2 (w/ English translation).

* cited by examiner

PLATELET-DERIVED MICROPARTICLES AS A NOVEL DIAGNOSIS MAKER FOR A CARDIOVASCULAR DISEASE

THE FIELD OF THE INVENTION

The present invention relates to a novel diagnosis maker for a cardiovascular disease comprising platelet-derived microparticles.

BACKGROUND OF THE INVENTION

Platelet-derived microparticles (PDMPs) are released from platelets in association with platelet activation, the contents of which include platelet granular proteins such as P-selectin, and various platelet surface membrane glycoproteins such as glycoprotein (GP)Ib/IX or GPIIb/IIIa[1]. PDMPs are not merely a marker for platelet activation but also have procoagulant activity, and thereby, contribute to thrombus formation[2]. In addition, PDMPs participate in the inflammatory process as a mediator of platelet-leukocyte, leukocyte-endothelial cell or leukocyte-leukocyte interactions[1]. PDMPs stimulate cytokine production and enhance the expression of cell adhesion molecules including leukocyte integrin Mac-I (CD 11 b/CD18, $\alpha M\beta 2$)[3]. Although PDMPs are usually determined by flow cytometry, circulating PDMPs are also measured by enzyme-linked immunosorbent assay (ELISA) using two antibodies against the platelet membrane surface glycoproteins, GPIb and GBIX[4]. Despite increased research activity on the characteristics of PDMPs, the clinical significance of the measurement of circulating PDMPs has not yet been established.

Percutaneous coronary intervention (PCI) produces significant inflammatory reaction in the injured vessel wall, which triggers acute ischemic events and late restenosis5, 6. In the process of inflammation at the site of PCI-induced injury, the activation of leukocytes, neutrophils as well as monocytes, and their interaction with platelets mediated by cell adhesion molecules are known to play an important causative role in the development of restenosis. There is increasing evidence that the interaction between platelets and leukocytes across an adherent layer of platelets precedes diapedesis and the infiltration of inflammatory cells into the PCI-injured vessel wall, which is denuded of vascular endothelial cells by balloon inflation or stenting7, 9. Among various adhesion molecules, leukocyte Mac-1 is of particular importance in the process of transplatelet migration. Mac-1 orchestrates the recruitment of leukocytes by binding to platelet ligands, such as GPIbα 10, to promote firm adhesion at sites of vessel wall injury. Monoclonal antibody blockade 11 and the absence of Mac-1 12 reduce neointimal thickening after experimental angioplasty and stenting. The inventors demonstrated previously that PCI-induced activation and up-regulation of Mac-1 on the surface of neutrophils reached a maximum 48 hrs after PCI and was associated with restenosis 13-18

Since GPIbα, a platelet ligand for leukocyte Mac-1, is expressed on the surface of PDMPs, the inventors hypothesized that circulating PDMPs could be linked to Mac-1 expressed on the surface of leukocytes, and could play an important role in the process of inflammation associated with arteriosclerosis.

SUMMARY OF THE INVENTION

In the present invention, to establish the clinical significance of circulating PDMPs, the inventors evaluated serial changes in the plasma concentration of PDMPs before and after PCI, and assessed the relation between PDMPs and activation of Mac-1 on the surface of neutrophils in the post-PCI inflammatory process. The inventors also investigated serial changes in high-sensitive C-reactive protein (hs-CRP) and activated Mac-1 on the surface of neutrophils. PDMPs, hs-CRP and activated Mac-1 increased after coronary stenting in a time-dependent manner. These changes were less striking in the peripheral blood. The value of PDMPs was correlated with hs-CRP levels and the relative increase in activated Mac-1 in coronary sinus blood after coronary stenting. The PDMP values, hs-CRP levels and relative increase in activated Mac-1 after coronary stenting were all associated with angiographic late lumen loss.

These results suggest that coronary stenting enhanced circulating PDMPs in association with an inflammatory response in the injured vessel wall. PDMPs may be a useful marker for evaluation of stent-induced inflammatory status and a sound surrogate marker for activated Mac-1. Furthermore, PDMPs may be also useful marker for inflammation-related cardiovascular diseases such as atherosclerosis.

In one aspect of the invention, a novel diagnosis maker for a cardiovascular disease comprising platelet-derived microparticles is provided.

In another aspect of the invention, it is provided that a method for diagnosing a cardiovascular disease in a subject with symptoms of cardiovascular disease or suspected of having cardiovascular disease, wherein said method comprises:

(a) obtaining a sample from said subject; reacting an antibody to platelet-derived microparticles or a fragment thereof with a biological sample;

(b) detecting a presence or an absence of the platelet-derived microparticles or a fragment thereof in said sample; and (c) diagnosing circulatory disease in said subject having said symptoms when said platelet-derived microparticles or a fragment thereof are detected in said sample.

In a further aspect of the invention, it is provided that a method for evaluating prognosis of cardiovascular disease in a subject with symptoms of cardiovascular disease or suspected of having cardiovascular disease, wherein said method comprises:

(a) obtaining a sample from said subject;

(b) reacting an antibody to platelet-derived microparticles or a fragment thereof with a biological sample;

(c) detecting a presence or an absence of the platelet-derived microparticles or a fragment thereof in said sample; and (d) evaluating prognosis of cardiovascular disease in said subject having said symptoms when said platelet-derived microparticles or a fragment thereof are detected in said sample.

In another aspect of the invention, it is provided that a method for evaluating whether cardiovascular disease has progressed in a patient having symptoms of said disease and already diagnosed as having said disease, wherein said method comprises:

(a) obtaining a sample from said subject;

(b) reacting an antibody to platelet-derived microparticles or a fragment thereof with a biological sample;

(c) detecting a presence or an absence of the platelet-derived microparticles or a fragment thereof in said sample; and (d) evaluating that said cardiovascular disease has progressed in said subject when said platelet-derived microparticles or a fragment thereof are detected in said sample.

In the above methods, said sample may be selected from the group consisting of blood, serum, cell and tissue. In above methods, said cardiovascular disease is selected from the group consisting of arterial hypertension, orthostatic hypotension and syncope, arteriosclerosis, coronary artery disease, heart failure, shock, arrhythmias, cardiac and respiratory arrest and cardiopulmonary resuscitation, valvular heart disease, endocarditis, pericardial disease, cardiac tumors, diseases of the aorta and its branches, peripheral vascular disorders, cerebrovascular disease, diabetic vascular disorders, or hyperlipidemia, and from the high risk group of potentially having these disorders.

DETAILED DESCRIPTION OF THE INVENTION

The present invention relates to a novel diagnosis maker for a cardiovascular disease comprising platelet-derived microparticles.

Inflammation as well as platelet activation at the site of local vessel-wall injury plays an essential role in the mechanism of restenosis after percutaneous coronary intervention (PCI). Platelet-derived microparticles (PDMPs) released from activated platelets are thought to play a role in the inflammatory process, interacting with leukocyte integrin Mac-1.

The present inventors serially measured circulating PDMPs by ELISA in 35 patients undergoing coronary stenting. Inventors also investigated serial changes in high-sensitive C-reactive protein (hs-CRP) and activated Mac-1 on the surface of neutrophils. PDMPs, hs-CRP and activated Mac-1 increased after coronary stenting in a time-dependent manner with the maximum response at 48 hr in coronary sinus blood (PDMPs: $10.2\pm5.7$ to $30.4\pm14.6$ U/ml; $P<0.001$, hs-CRP: $0.26\pm0.22$ to $1.51\pm0.88$ mg/dl; $P<0.001$, activated Mac-1, $138\pm17\%$ relative increase, $P<0.001$). These changes were less striking in the peripheral blood. The value of PDMPs was correlated with hs-CRP levels ($R=0.58$, $P<0.001$) and the relative increase in activated Mac-1 ($R=0.69$, $P<0.001$) in coronary sinus blood 48 hrs after coronary stenting. The PDMP values, hs-CRP levels and relative increase in activated Mac-1 at 48 hr after coronary stenting were all associated with angiographic late lumen loss.

These results suggest that coronary stenting enhanced circulating PDMPs in association with an inflammatory response in the injured vessel wall. PDMPs may be a useful marker for evaluation of stent-induced inflammatory status and a sound surrogate marker for activated Mac-1.

Platelet-derived microparticles (PDMP(s)) refer to microparticles released from platelets in association with platelet activation, the contents of which include platelet granular proteins such as P-selectin, and various platelet surface membrane glycoproteins such as glycoprotein (GP)Ib/IX or GPIIb/IIIa1. PDMPs are not merely a marker for platelet activation but also have pro-coagulant activity, and thereby, contribute to thrombus formation. In addition, PDMPs participate in the inflammatory process as a mediator of platelet-leukocyte, leukocyte-endothelial cell or leukocyte-leukocyte interactions. PDMPs stimulate cytokine production and enhance the expression of cell adhesion molecules including leukocyte integrin Mac-1(CD11b/CD18, $\alpha M\beta 2$)3. Although PDMPs are usually determined by flow cytometry, circulating PDMPs are also measured by enzyme-linked immunosorbent assay (ELISA) using two antibodies against the platelet membrane surface glycoproteins, GPIb and GBIX4.

In the present invention, the inventors demonstrated that circulating levels of PDMPs, hs-CRP levels, and 8B2 binding on the surface of neutrophils increased in a time-dependent manner after coronary stenting with the maximum increase at 48 hr. Furthermore, these changes were more striking in the coronary sinus than in the peripheral blood and the PDMP levels at 48 hr were correlated with the hs-CRP levels at 48 hr and more closely with increase in 8B2 binding at 48 hr versus baseline in the coronary sinus. In addition, these three parameters were associated with angiographic late lumen loss (i.e., neo-intimal thickening after coronary stenting). These results indicated that the PDMPs increased in the coronary circulation, and were associated with Mac-1 activation on the surface of neutrophils in relation to stent-induced inflammatory response, possibly at sites of PCI-induced injury.

The cardiovascular disease includes, but are not limited to, arterial hypertension, orthostatic hypotension and syncope, arteriosclerosis, coronary artery disease, heart failure, shock, arrhythmias, cardiac and respiratory arrest and cardiopulmonary resuscitation, valvular heart disease, endocarditis, pericardial disease, cardiac tumors, diseases of the aorta and its branches, peripheral vascular disorders, cerebrovascular disease, diabetic vascular disorders, or hyperlipidemia, and the like, and also the high risk group of potentially having these disorders. Arteriosclerosis is mostly preferred for the present invention.

Detection for a diagnosis of cardiovascular disease, or an evaluation of prognosis or progress of cardiovascular disease is performed by immunologic assays using antibodies to PDMPs or a fragment thereof and samples from subjects in need of such diagnosis. Thus the method of the invention includes methods that detect PDMPs in a sample, for example, in a non-specific manner or in a specific manner, and then detecting such non-specific or specific binding.

The above examples of methods are not the only methods by which one skilled in the arts of medicine, microbiology, and immunology may use the invention. Any method that allows determination of an interaction of the immune system with PDMPs in a sample is useful in the method of the invention.

According to the method of the invention, a diagnosis of cardiovascular disease in a patient suspected of having such disease, or an evaluation of the severity or progression of cardiovascular disease in a patient already diagnosed as having the same, is made by detecting an immune response against PDMPs in a sample from the patient in need of such diagnosis. When it is desired to detect PDMPs, generally and preferably, PDMPs in the patient's sample are detected.

The detection of PDMPs can be performed by directly detecting the binding of such antibodies to PDMPs. Alternatively, the detection of antibodies that bind to PDMPs can be performed by indirectly detecting the binding of such antibodies to PDMPs.

The term "antibodies" in meant to include both the native antibodies, and biologically active derivatives of antibodies, such as, for example, Fab', F(ab')2 or Fv as well as single-domain and single-chain antibodies. A biologically active derivative of an antibody retains the ability to bind an antigen.

The PDMPs in the patient's sample, and especially in blood, serum, cell or tissue sample, can be detected in immunoassays wherein the PDMPs can be utilized in liquid phase or bound to a solid phase carrier. The preferred immunoassays for detecting PDMPs using the methods of this invention include radioimmuno-assays, enzyme-linked immunosorbent assays (ELISA), or other assays known in the art, such as immunofluoscent assays, chemiluminescent assays, or bioluminescent assays. The preferred immunoassay for detecting the PDMPs is ELISA assay.

Circulating PDMPs as a Marker of Platelet Activation

PDMPs have been widely measured by flow cytometry and investigated extensively. Although the significance of elevated PDMP levels remains controversial, many clinical disorders are associated with elevated PDMP levels 1, 2, 21-24. Elevated PDMPs are observed in patients with acute coronary syndrome (ACS) in relation to platelet activation 23. Gawaz et al. 24 examined various aspects of platelet activation in patients with acute myocardial infarction undergoing direct PCI and demonstrated that PDMPs were significantly enhanced after PCI. However, PDMPs measure by ELISA, as in the present invention, may have different clinical features from those detected by flow cytometry. Nomura et al 26 observed serial changes in PDMPs measured by ELISA after PCI in ACS patients and demonstrated that PDMP levels decreased significantly 4 days after PCI. Their results are contrary to ours that showed increased PDMPs with the maximum increase 48 hr after PCI. This discrepancy may be attributed to differences in the present invention populations. The study by Nomura et al. selected only ACS patients whose platelets had already been activated before PCI and the activation status was stabilized 4 days after PCI, while the present invention included patients with stable angina alone without platelet activation at baseline before PCI. The time course of PDMP changes that inventors observed indicated that stable platelets were activated by PCI with the maximum activation at 48 hr, which is consistent with the time course of P-selectin changes post-PCI that has been previously reported by us as well as others.

A Role for PDMPs in the Post-PCI Inflammatory Process

The activation of leukocytes, neutrophils and monocytes is known to play an important causative role in the post-PCI inflammatory process that leads to the development of restenosis 27-30. Activated leukocytes transmigrate and infiltrate into the PCI-injured vessel wall and produce various cytokines, growth factors, free radicals, and proteolytic enzymes, leading to neointimal thickening and restenosis. At the PCI-injured vessel wall, which is denuded of vascular endothelial cells by balloon inflation or stenting, platelets first adhere to the vessel surface and the platelet layer is formed. Leukocytes adhere to the platelet layer and then migrate into the vessel wall—namely, transplatelet leukocyte migration 9, 31, 32. In the process of transplatelet leukocyte migration, platelet surface P-selectin binds to P-selectin glycoprotein ligand (PSGL)-1 on the surface of leukocytes and mediates the rolling attachment of leukocytes with the platelet layer 33, 34. In addition, subsequent firm adhesion of leukocytes is mediated by Mac-1, which is expressed on activated leukocytes and binds to ligands such as fibrinogen 9, 33 GPIbα10, intercellular adhesion molecules (ICAM)-29, or junctional adhesion molecules (JAM)-3 35. Among these platelet ligands for Mac-1 binding, Simon et al. especially focused on GPIbα as the most important ligand in the mechanism of transplatelet leukocyte migration in the vessel wall injured by PCI. Evangelista et al. 33, 34 demonstrated in-vitro that the binding of P-selectin to PSGL-1 triggers tyrosine kinase-dependent signaling that leads to functional up-regulation or activation of Mac-1. In this way, an adhesion cascade appears to occur with considerable crosstalk between P-selectin and Mac-1 in the process of platelet-leukocyte interaction 9, 33. Moreover, Forlow et al. 36 reported, that P-selectin-expressing PDMPs bind to leukocytes that express PSGL-1, suggesting that PDMPs can mediate leukocyte-leukocyte interaction leading to leukocyte aggregation and accumulation at the injured surface of the vessel surface, especially when the number of PDMPs increased. Thus, the measurement of PDMPs may be useful for investigating this pathophysiological process. In addition, in the PDMP ELISA assay system, the inventors used an antibody against GPIbα for detecting PDMPs4. Considering that GPIbα is the key ligand for Mac-1 in transplatelet leukocyte migration, PDMPs detected by ELISA may be a surrogate for leukocyte Mac-1 activity. Our clinical finding of a close correlation between PDMPs at 48 hr and the increase over baseline in activated Mac-1 on the surface of neutrophils at 48 hr supports this hypothesis.

Potential Limitations

The present invention has several potential limitations. Although PDMPs are not the only products of platelet activation but also their own function such as procoagulant activity and participants in the inflammatory process as a mediator of platelet-leukocyte interaction, circulating PDMPs detected by ELISA assay are likely to be a residue of activated PDMPs that adhere to leukocytes. 4 Therefore, assigning a pathophysiological role to PDMPs in the vascular injury, inflammation and repair response remains speculative, but highly likely in light of our observations showing the relationship between PDMPs, CRP, and Mac-1 activity after PCI or the relationship between those and angiographic late lumen loss. Furthermore, PDMPs, easily measured by ELISA, may serve as a useful surrogate of activated Mac-1 that can only be measured with a complex technique such as flow cytometry.

Clinical Implications: Conclusion

Restenosis, the most significant problem with PCI, has been markedly reduced since the introduction of coronary stents. Recent advances in drug-eluting stents have further reduced the restenosis rate to less than 10%. However, even drug-eluting stents are not perfect and have several serious problems such as long-term prognosis or late incomplete apposition. Thus, the issue of restenosis has not been completely resolved and the inventors should continue to develop approaches to further reduce restenosis.

Recent chemical, biological or pharmacological approaches to prevent restenosis include two strategies, an 'anti-proliferative' strategy and an 'anti-inflammatory' strategy. Most novel approaches for reducing restenosis, including newly developed drug-eluting stents, have employed an 'anti-proliferative' strategy. For further restenosis reduction, the inventors have proposed an 'anti-inflammatory strategy', which appears to be a rational therapeutic strategy for preventing restenosis. In addition, the inventors can envision a significant clinical advantage of Mac-1-guided therapy for reducing restenosis, in which PDMPs measured by ELISA would serve as a sound surrogate marker for activated Mac-1.

EXAMPLES

Methods

Sample Preparation

The subjects included 35 patients with atherosclerotic coronary artery disease who underwent single elective coronary stent implantation for a proximal left anterior descending artery (LAD) lesion. The patients' characteristics are shown in Table 1. To reduce the heterogeneity of the population, the inventors excluded patients with poorly-controlled diabetes mellitus, hypertension or hyperlipidemia, or with a systemic inflammatory reaction as shown by a baseline CRP >1.5 mg/dL. All of the patients received standard daily oral medications for angina, including 81 mg of aspirin, and none of these medications were discontinued or exchanged during PCI or the post-PCI follow-up period. The patients received 200 mg of daily oral ticlopidine 2 days before PCI as a specific post-stent anti-platelet regimen and this therapy was continued for one month after PCI. Coronary stent implantation was performed using the standard Judkins technique from a femoral approach. Intravenous heparin was administered to maintain an adequate activated clotting time (ACT) during the procedure and for 48 hrs after PCI. Follow-up angiography was recommended for all patients at 6 months after angioplasty, and was performed earlier if clinically indicated. Coronary lesions were assessed by quantitative coronary angiographic (QCA) measurements and late lumen loss (minimal lumen diameter after PCI minus minimal lumen diameter at follow-up angiography) was calculated as an index of neointimal thickening. Prior to PCI, a coronary sinus catheter was positioned in the coronary sinus and left for 48 hr after the procedure for coronary sinus blood sampling. Coronary sinus blood as well as peripheral blood was collected before PCI and 15 min after, 24 hr after, and 48 hr after coronary stenting. Whole blood was immediately collected into tubes containing acid citrate dextrose (ACD), ethylene diaininetetraacetate (EDTA), or both (ACD/EDTA). The study protocol was approved by the local institutional review board, and written informed consent was obtained from each patient.

Laboratory Measurements

The ACD/EDTA blood was centrifuged at 5000×g for 20 min, plasma was withdrawn and stored at −80° C. until assay. The assay for circulating PDMPs was performed using enzyme-linked immunosorbent assay (ELISA), as previously reported.4 Briefly, 50 µl of samples or standard were added to each well of 96-well microtiter plates coated with antibody against platelets and GPXI (MKP-9) and incubated for 18 hrs at 25° C. on a plate shaker (200 rpm). Plates were washed 3 times with 350 µl/well of buffer (0.05% Tween 20 in PBS). Fifty µl of biotinylated antibody against platelet GPIbα (NNKY5-5) (0.2 µl/ml in 1% nonfat milk/PBS) was added to each well and incubated for 2 hrs at 25° C. on a plate shaker. After each well was washed 3 times with 350 µl of buffer, 50 µl of peroxidase-conjugated avidin (diluted 1:20000 in 1% nonfat dry milk, PBS; Vector Laboratories, Burlingame, Calif.) was added to each well and incubated for 2 hrs at 25° C. on a plate shaker. Each well was subsequently washed 3 times with 350 µl of buffer and then incubated with 100 µl peroxidase substitute solution (ScyTek, Logan, Utah) for 20 min at room temperature. After this incubation, stop solution (SkyTec) was added to each well, and the absorbance was measured with an ELISA reader at 450 nm.

The EDTA blood was centrifuged at 1,500×g for 15 min at room temperature for the measurement of high-sensitive (hs)-CRP. The plasma was frozen and stored at −80° C. until analysis. The hs-CRP level was measured by particle-enhanced technology on the Behring BN II nephelometer (Dade Behring Inc., Newark, Del.) 19. This assay used monoclonal anti-CRP antibodies and a calibrator that was also traceable to WHO Reference Material.

The ACD whole blood was used for flow cytometric analysis for expression of activation-dependent neoepitope of Mac-1 on the surface of neutrophils. The inventors used a purified monoclonal antibody, 8B2 (provided by Dr. Thomas Edgington, Department of Immunology, The Scripps Research Institute, La Jolla, Calif.), with a high sensitivity and specificity for the recognition of the activation-dependent neo-epitope of Mac-1 18, 20. Purified mouse immunoglobulin (Ig) G1 was also used as an isotype-negative control. The fluorescein-conjugated second-step reagents for indirect immunofluorescence were fluorescein isothiocyanate (FITC)-conjugated F(ab')2 fragment of anti-mouse IgG goat immunoglobulins (Dako, Glostrup, Denmark). Indirect immunofluorescence labeling was performed on whole blood incubated with 8B2 (100 µg/ml). Then, the flow cytometric analysis for 8B2 binding (activated Mac-1) was performed using an EPICS XL flow cytometer (Coultronics, Sunnyvale, Calif.). Mean channel fluorescence intensity (MFI) was calculated as an index of activated Mac-1 on the surface of neutrophils.

Statistical Analysis

Values were expressed as the mean±SD. In both studies, inter-group comparisons were performed using Student's unpaired t test for continuous variables. Serial changes in the variables were evaluated by repeated measures analysis of variance (ANOVA), for intra- and inter-group comparisons. Correlations between two parameters were assessed using simple linear regression. $P<0.05$ was considered to be significant.

Results

Patients' Characteristics and Baseline Values Before Coronary Stenting

Baseline circulating PDMPs, hs-CRP and MFI for 8B2 binding before PCI in the peripheral blood was independent of age, gender, the presence of multivessel disease, coronary risk factors, or medications possibly affecting inflammation such as statins or angiotensin receptor blockers (Table 2).

Figure 1:
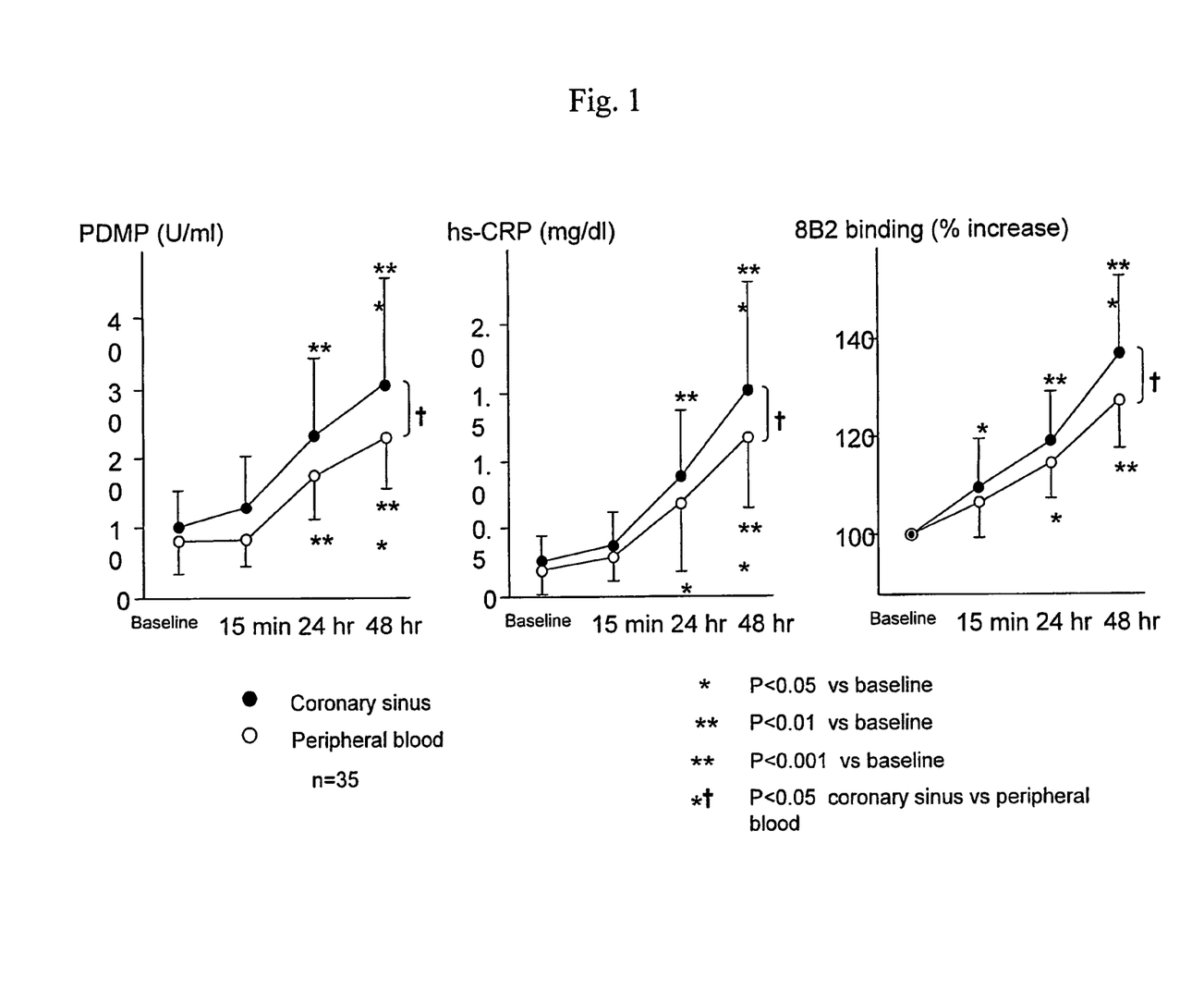
FIG. 1. Serial changes in circulating levels of PDMPs (right), plasma hs-CRP level (mid) and MFI for 8B2 binding on the surface of neutrophils (left). These 3 parameters increased in a time-dependent manner after coronary stenting reaching a maximum at 48 hrs. The changes were more striking in coronary sinus than peripheral blood.

Serial Change in Circulating PDMPs, hs-CRP Levels, and Activated Mac-1 on the Surface of Neutrophils after Coronary Stenting Serial changes in circulating levels of PDMPs were observed. Although no change was evident 15 min after stenting, an increase was noted after 24 hr in both coronary sinus and peripheral blood. The maximal increase was seen at 48 hr (coronary sinus: 10.2±5.7 to 30.4±14.6 U/ml, $P<0.001$; peripheral blood: 8.8±6.2 to 22.6±8.4 U/ml, $P<0.001$). The changes were more striking in coronary sinus blood than in peripheral blood ($P<0.05$) (FIG. 1, left).

The plasma hs-CRP levels also increased after coronary stenting from baseline values in the same manner as the PDMPs, reaching a maximum at 48 hrs in both coronary sinus blood (0.26±0.22 to 1.51±0.88 mg/dl, $P<0.001$) and peripheral blood (0.22±0.21 to 1.22±0.49 mg/dl, $P<0.001$). The changes in hs-CRP levels were also more striking in coronary sinus blood than in peripheral blood ($P<0.05$) (FIG. 1, mid).

The MFI for 8B2 binding (i.e., expression of Mac-1 activation neoepitope on the surface of neutrophils) began to increase 15 min after coronary stenting and reached a maximum at 48 hr in both coronary sinus and peripheral blood. The relative increases compared to baseline at 15 min, 24 hr and 48 hr in coronary sinus blood were 108±12% (P<0.05), 119±11% (P<0.01) and 138±17% (P<0.001), respectively. The increases in peripheral blood were 106±8% (NS), 114±8% (P<0.05) and 127±12% (P<0.01), respectively. The change in 8B2 binding capacity was also more striking in coronary sinus blood than in peripheral blood (P<0.05) (FIG. 1, right).

The Relation Between PDMPs, hs-CRP and Activated Mac-1 at 48 hr

Figure 2:
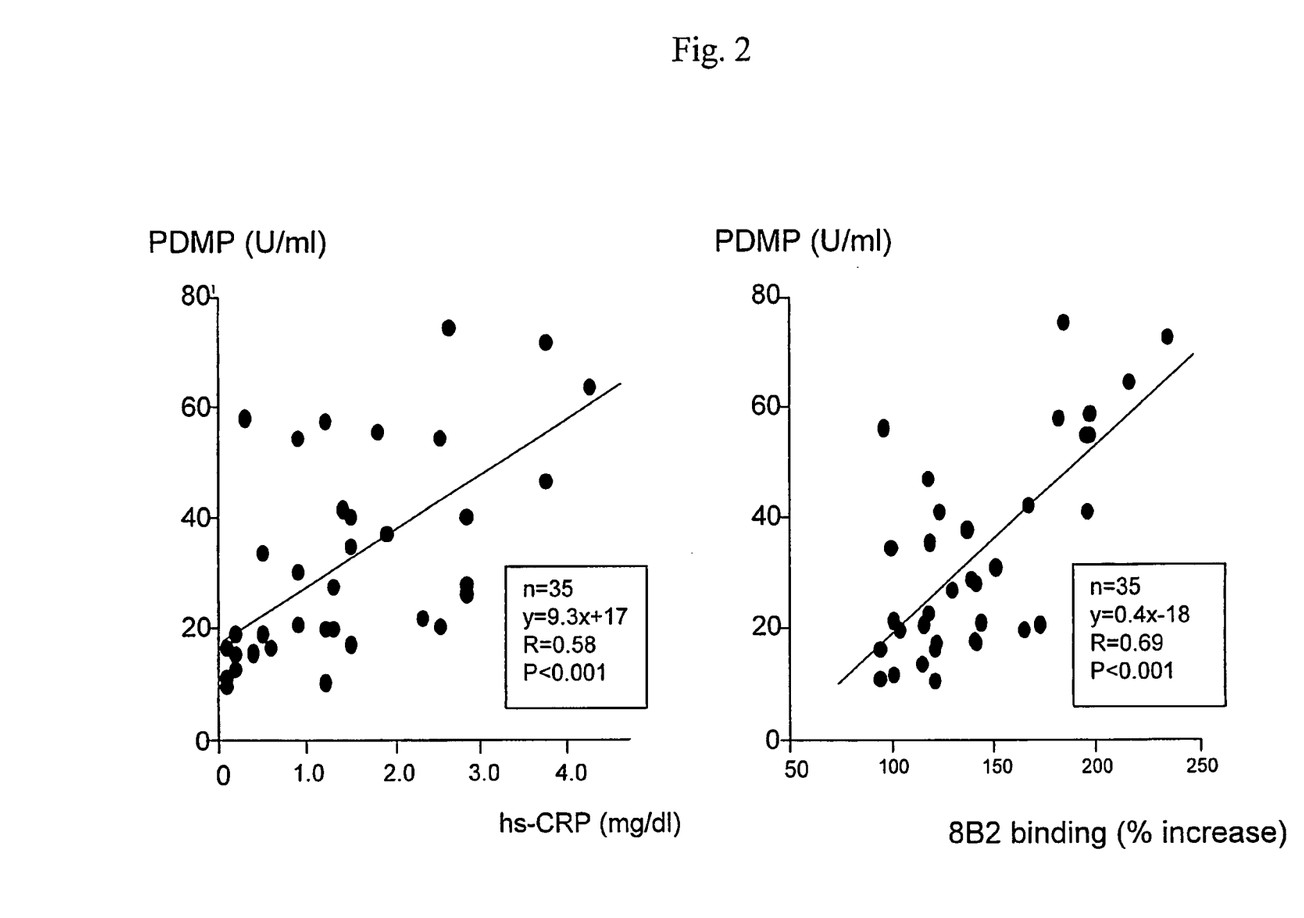
FIG. 2. Correlation between PDMPs level at 48 hr and hs-CRP level at 48 hr, or relative increase in 8B2 binding at 48 hr versus baseline in the coronary sinus. The PDMPs were positively correlated with hs-CRP and more closely correlated with the increase in 8B2 binding.

The circulating PDMPs at 48 hr were positively correlated with hs-CRP levels at 48 hr (r=0.58, P<0.001) and more closely correlated with the relative increase in 8B2 binding on the surface of neutrophils at 48 hr compared to baseline (r=0.69, P<0.00) in coronary sinus blood (FIG. 2).

Figure 3:
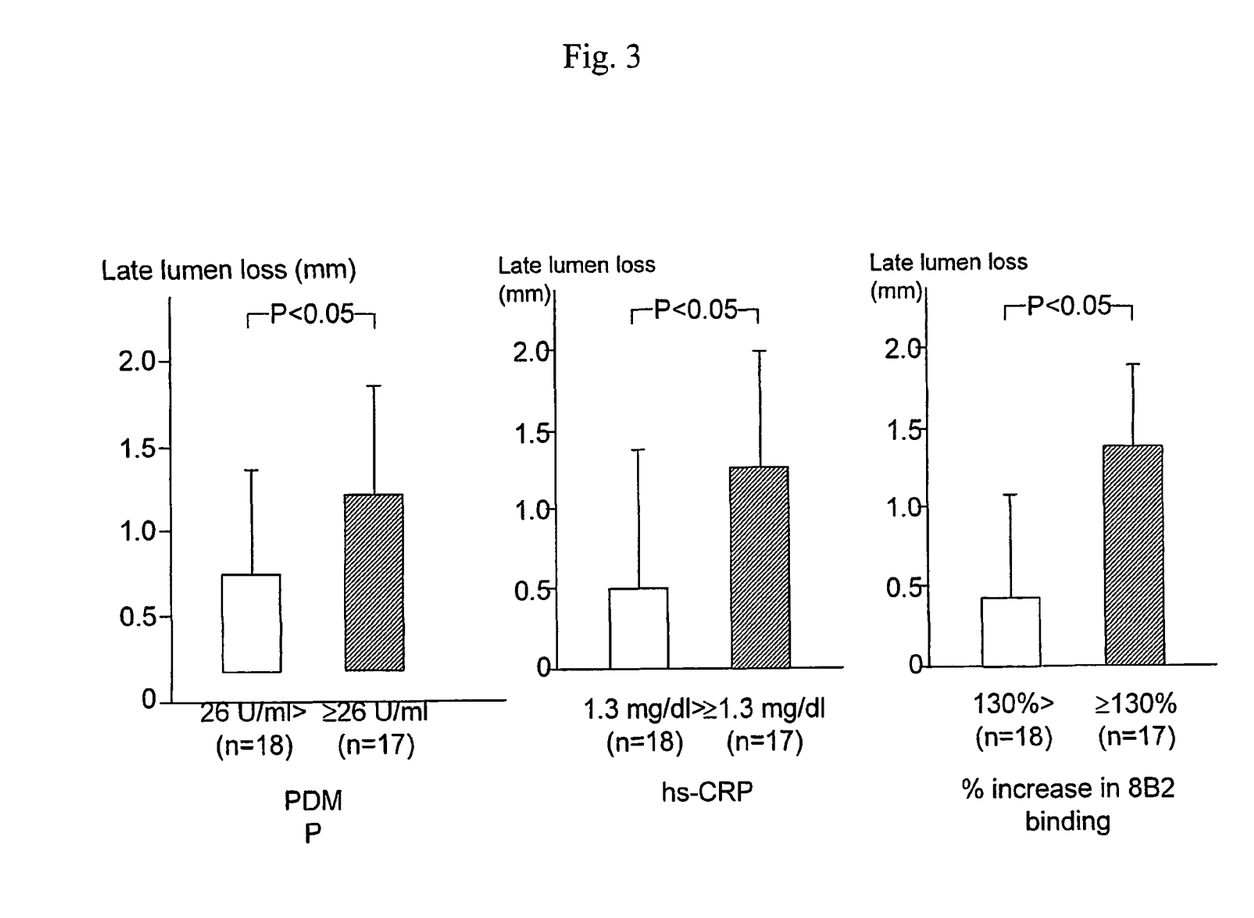
FIG. 3. Associations of PDMPs level at 48 hr, hs-CRP level at 48 hr, and the relative increase in 8B2 binding at 48 hr with angiographic late lumen loss. Using the median values of PDMPs (26 µg/ml), hs-CRP (1.3 mg/dl) and the relative increase in 8B2 binding (130%), patients were divided into two groups for each parameter. The high-value group included values than the median while the low-value group included values <than the median. Angiographic late lumen loss was greater in the high-value group than in the low-value group for each parameter.

The Relation Between Late Lumen Loss and PDMPs, Hs-CRP and Activated Mac-1 at 48 hr Using the median values of PDMPs (26 U/ml), hs-CRP (1.3 mg/dl) and the relative increase in 8B2 binding (130%) at 48 hr in all of the patients, the patients were divided into two groups for each parameter. The high-value group included values than the median while the low-value group included values <than the median. Angiographic late lumen loss was greater in the high-value group than in the low-value group for PDMPs (1.22±0.67 vs 0.62±0.64 mm, P<0.05), hs-CRP (1.26±0.71 vs 0.49±0.95 mm, P<0.05) and the increase in 8B2 binding (1.42±0.39 vs 0.44±0.76 mm, P<0.05) (FIG. 3).

TABLE 1

| Patients' Characteristics | |
| --- | --- |
| Age | 44-75 (62 ± 8) |
| Men/Women | 27/8 |
| SVD/MVD | 18/17 |
| | 30 (86%) |
| Smoking | 8 (23%) |
| Diabetes | 21 (60%) |
| Hypertension | 167-262 (207 ± 28) |
| Total Cholesterol (mg/dl) | 51-504 (171 ± 115) |
| | 22-86 (50 ± 16) |
| Triglyceride (mg/dl) | 90-194 (128 ± 30) |
| HDL-cholesterol (mg/dl) | 10 (29%) |
| LDL-cholesterol (mg/dl) | 4 (11%) |
| | 18 (51%) |

AP, angina pectoris;
OMI, old myocardial infarction;
SVD, single vessel coronary artery disease;
MVD, multi-vessel coronary artery disease;
HDL, high-density lipoprotein;
LDL, low-density lipoprotein;
ACEI, angiotensin converting enzyme inhibitor; and
ARB, angiotensin receptor blocker.

TABLE 2

Patients' Characteristics and Baseline Values

| | Patients | PDMP (U/ml) | | | hs-CRP (mg/dl) | | | MFI for 8B2 (×10$^3$) | | |
| --- | --- | --- | --- | --- | --- | --- | --- | --- | --- | --- |
| | Yes/no | Yes | No | P | Yes | No | P | Yes | No | P |
| Age > 63 | 18/17 | 9.4 ± 6.2 | 8.2 ± 7.4 | N S | 0.22 ± 0.32 | 0.22 ± 0.36 | N S | 1.22 ± 0.25 | 1.22 ± 0.31 | N S |
| Male gender | 27/8 | 9.2 ± 5.8 | 7.5 ± 6.8 | N S | 0.22 ± 0.28 | 0.22 ± 0.34 | N S | 1.24 ± 0.32 | 1.15 ± 0.64 | N S |
| MVD | 17/18 | 9.2 ± 6.7 | 8.3 ± 7.4 | N S | 0.24 ± 0.34 | 0.20 ± 0.38 | N S | 1.23 ± 0.24 | 1.21 ± 0.31 | N S |
| Smoking | 30/5 | 8.8 ± 5.9 | 8.8 ± 6.4 | N S | 0.23 ± 0.21 | 0.16 ± 0.62 | N S | 1.22 ± 0.34 | 1.22 ± 0.21 | N S |
| Diabetes | 8/27 | 9.8 ± 8.4 | 8.5 ± 5.9 | N S | 0.29 ± 0.48 | 0.20 ± 0.16 | N S | 1.23 ± 0.42 | 1.22 ± 0.24 | N S |
| Hypertension | 21/14 | 8.8 ± 6.4 | 8.7 ± 7.2 | N S | 0.22 ± 0.30 | 0.22 ± 0.25 | N S | 1.20 ± 0.42 | 1.25 ± 0.44 | N S |
| LDL-cholesterol > 140 mg/dl | 10/25 | 9.0 ± 4.8 | 8.7 ± 7.4 | N S | 0.24 ± 0.28 | 0.21 ± 0.38 | N S | 1.25 ± 0.35 | 1.21 ± 0.38 | N S |
| Statin | 10/25 | 8.6 ± 5.8 | 8.9 ± 8.2 | N S | 0.20 ± 0.39 | 0.33 ± 0.18 | N S | 1.20 ± 0.64 | 1.23 ± 0.25 | N S |
| ACEI | 4/31 | 7.5 ± 11.2 | 9.0 ± 6.4 | N S | 0.32 ± 0.52 | 0.21 ± 0.22 | N S | 1.24 ± 0.34 | 1.22 ± 0.24 | N S |
| ARB | 18/17 | 8.6 ± 6.2 | 8.9 ± 6.6 | N S | 0.21 ± 0.32 | 0.23 ± 0.24 | N S | 1.20 ± 0.27 | 1.24 ± 0.34 | N S |

PDMP, platelet-derived microparticle;

hs-CRP, high-sensitive C-reactive protein;

MFI, mean channel fluorescence intensity;

NS, not significant;

MVD, multivessel disease.

The following documents cited herein are incorporated by reference throughout the specification.

REFERENCES

1 Nomura S. Function and clinical significance of platelet-derived microparticles. Int J Hematol 2001; 74: 397-404
2 Sims P J, Faioni E M, Wiedmer T, et al. Complement proteins C5b-9 cause release of membrane vesicles from the platelet surface that are enriched in the membrane receptor for coagulation factor Va and express prothrombinase activity. J Biol Chem 1988; 263: 18205-18212.
3 Barry O P, Pratico D, Savani R C, et al. Modulation of monocyte-endothelial cell interaction by platelet microparticles. J Clin Invest 1998; 102: 136-144.
4 Osumi K, Ozeki Y, Saito S, et al. Development and assessment of enzyme immunoassay for platelet-derived microparticles. Thromb Haemost 2001; 85: 326-330.
5 Cole C W, Hagen P-Q, Lucas J F, et al. Association of polymorphonuclear leukocytes with sites of aortic catheter-induced injury in rabbits. Atherosclerosis. 1987; 67: 229-236.
6 De Servi S, Mazzone A, Ricevuti G, et al. Granulocyte activation after coronary angioplasty in human. Circulation. 1990; 82: 140-146.
7 Kuijper P H, Gallardo Torres H I, et al. Platelet-dependent primary hemostasis promotes selectin- and integrin-mediated neutrophil adhesion to damaged endothelium under flow condition. Blood. 1996; 87:3271-3281.
8 Hagberg I A, Roald H E, Lyberg T. Adhesion of leukocytes to growing arterial thrombi. Thromb Haemost. 1998; 80:852-858.
9 Diacovo T G, Roth S J, Buccola J M, et al. Neutrophil rolling, arrest, and transmigration across activated, surface-adherent platelets via sequential action of P-selectin and the 132 integrin CD11b/CD18. Blood. 1996; 88:146-157.
10 Simon D I, Chen Z, Xu H, Li C Q, et al. Platelet glycoprotein Iba is a counterreceptor for the leukocyte integrin Mac-1 (CD I 1 b/CD 18). J Exp Med. 2000; 192:193-204.
11 Rogers C, Edelman E R, Simon D I. A mAb to the (32-leukocyte integrin Mac-1 (CD11b/CD18) reduces intimal thickening after angioplasty or stent implantation in rabbits. Proc Natl Acad Sci USA. 1998; 95:10134-10139.
12 Simon D I, Chen Z, Seifert P, et al. Decreased neointimal formation in Mac-1-/-mice reveals a role for inflammation in vascular repair after angioplasty. J Clin Invest. 2000; 105: 293-300.
13 Newmann F J, Ott I, Gawaz M, et al. Neutrophil and platelet activation at balloon-injured coronary artery plaque in patients undergoing angioplasty. J Am Coll Cardiol. 1996; 27: 819-824.
14 Inoue T, Sakai Y, Morooka S, et al. Expression of polymorphonuclear leukocyte adhesion molecules and its clinical significance in patients treated with percutaneous transluminal coronary angioplasty. J Am Coll Cardiol. 1996; 28:1127-1133.
15 Inoue T, Sakai Y, Fujito T, et al. Clinical significance of neutrophil adhesion molecule expression after coronary angioplasty on the development of restenosis. Thromb Haemost. 1998; 79:54-58.
16 Inoue T, Sakai Y, Hoshi K, et al. Lower expression of neutrophil adhesion molecule indicates less vessel wall injury and might explain lower restenosis rate after Cutting Balloon angioplasty. Circulation. 1998; 97:2511-2518.
17 Inoue T, Sohina R, Miyazaki T, et al. Activation process of platelets and neutrophils after coronary stent implantation: Comparison with balloon angioplasty. Am J Cardiol. 2000; 86:1057-1062.
18 Inoue T, Uchida T, Yaguchi I, et al. Stent-induced expression and activation of the leukocyte integrin Mac-1 is associated with neointimal thickening and restenosis. Circulation. 2003; 107: 1757-1763.
19 Ledue T B, Weiner D L, Sipe J, et al. Analytical evaluation of particle-enhanced immunonepherometric assays for C-reactive protein, serum amyloid A, and mannose binding protein in human serum. *Ann Clin Biochem.* 1998; 35: 745-753.
20 Elemer G S, Edgington T S. Two independent sets of monoclonal antibodies define neoepitope linked to soluble ligand binding and leukocyte adhesion functions of activated αMβ2. *Circ Res.* 1994; 75: 165-171
21 Zucker-Franklin D, Karpatkin S. Red cell and platelet fragmentation in idiopathic thrombocytopenic purpura. N Engl J Med 1977; 297: 517-523.
22 Jy W, Horstman L L, Janania J, et al. Elevated platelet microparticles in transient ischemic attacks, lacunar infarcts, and multiinfarct dementias. Thromb Res. 1996; 72: 295-304.
23 Katopodis J N, Kolodny L, Jy W, et al. Platelet microparticles and calcium homeostasis in acute coronary ischemia. Am J Hematol 1997; 54: 95-101.
24 Nomura S, Imamura A, Okubo M, et al. Platelet-derived microparticles in patients with arteriosclerosis obliterans: enhancement of high shear-induced microparticle generation by cytokines. Thromb Res 2000; 98: 257-268.
25 Gawaz M, Newmann F-J, Ott I, et al. Platelet function in acute myocardial infarction treated with direct angioplasty. Circulation 1996; 93: 229-237.
26 Nomura S, Uehara S, Saito S, et al. Enzyme immunoassay detection of platelet-derived microparticles and RANTES in acute coronary syndrome. Thromb Haemost 2003; 89: 506-512.
27 Cole C W, Hagen P-O, Lucas J F, et al. Association of polyinorphonuclear leukocytes with sites of aortic catheter-induced injury in rabbits. Atherosclerosis. 1987; 67: 229-236.
28 De Servi S, Mazzone A, Ricevuti G, et al. Granulocyte activation after coronary angioplasty in human. Circulation. 1990; 82: 140-146.
29 Springer T A. Traffic signals for lymphocyte recirculation and leukocyte emigration: the multistep paradigm. Cell. 1994; 76: 301-314.
30 Newmann F J, Ott I, Gawaz M, et al. Neutrophil and platelet activation at balloon-injured coronary artery plaque in patients undergoing angioplasty. J Am Coll Cardiol. 1996; 27: 819-824.
31 Kuijper P H, Gallardo Torres H I, et al. Platelet-dependent primary heinostasis promotes selectin- and integrin-mediated neutrophil adhesion to damaged endothelium under flow condition. Blood. 1996; 87:3271-3281.
32 Hagberg I A, Roald H E, Lyberg T. Adhesion of leukocytes to growing arterial thrombi. Thromb Haemost. 1998; 80:852-858.
33 Evangelista V, Manalini S, Rotondo S, et al. Platelet/polymorphonuclear leukocyte interaction in dynamic conditions: Evidence of adhesion cascade and crosstalk between P-selectin and the 132 integrin CD11b/CD18. Blood. 1996; 88: 4183-4194.
34 Evangelista V, Manarini S, Sideri R, et al. Platelet/polymorphonuclear leukocyte interaction: P-selectin triggers protein-tyrosine phosphorylation-dependent CD11b/CD18 adhesion: role of PSGL-1 as a signaling molecule. Blood. 1999; 93: 876-885.

35 Santoso S, Sachs U J H, Kroll H, et al. The junctional adhesion molecule 3 (JAM-3) on human platelets is a counterreceptor for the leukocyte integrin Mac-1. J Exp Med. 2002; 196: 679-691.

36 Forlow S B, McEver R P, Nollert M U. Leukocyte-leukocyte interactions mediated by platelet microparticles under flow. Blood 2000; 95: 1317-1323.

What is claimed is:

1. A method for evaluating whether coronary artery disease has progressed in a patient previously diagnosed as having said disease and stable angina, wherein said method comprises:
   (a) obtaining a biological sample of coronary sinus blood from said patient at a first time point and a second time point;
   (b) detecting the level of platelet-derived microparticles (PDMPs) or a fragment thereof, in the first time point sample and the second time point sample with an antibody to PDMPs or a fragment thereof;
   wherein an increase in a level of the PDMPs in the second time point sample in comparison to a level in the first time point sample is indicative of progression of coronary artery disease; and
   wherein the level of PDMPs or a fragment thereof of $10.2\pm5.7$ to $30.4\pm14.6$ U/ml in said coronary sinus blood is indicative of progression of coronary artery disease.

2. The method of claim 1, farther comprising:
   detecting a level of C-reactive proteins, and leukocyte Mac-1 in the first and second time point samples, by reacting an antibody to C-reactive proteins and an antibody to leukocyte Mac-1,
   wherein an increase in the level of PDMPs, C-reactive proteins and leukocyte Mac-1 in the second time point sample in comparison to the level in the first time point sample is indicative of progression of coronary artery disease.

3. The method of claim 1, wherein the second time point sample is taken 24 hours after the first time point sample.

4. The method of claim 1, wherein the second time point sample is taken 48 hours after the first time point sample.

* * * * *